(12) United States Patent
Morrison

(10) Patent No.: US 10,799,655 B2
(45) Date of Patent: Oct. 13, 2020

(54) ULTRASONIC ENERGY MEASUREMENTS IN RESPIRATORY DRUG DELIVERY DEVICES

(71) Applicant: KONINKLIJKE PHILIPS N.V., Eindhoven (NL)

(72) Inventor: Mark Steven Morrison, Basking Ridge, NJ (US)

(73) Assignee: Koninklijke Philips N.V., Eindhoven (NL)

( * ) Notice: Subject to any disclaimer, the term of this patent is extended or adjusted under 35 U.S.C. 154(b) by 1072 days.

(21) Appl. No.: 14/903,723

(22) PCT Filed: Jun. 19, 2014

(86) PCT No.: PCT/IB2014/062449
§ 371 (c)(1),
(2) Date: Jan. 8, 2016

(87) PCT Pub. No.: WO2015/004553
PCT Pub. Date: Jan. 15, 2015

(65) Prior Publication Data
US 2016/0250426 A1    Sep. 1, 2016

Related U.S. Application Data

(60) Provisional application No. 61/844,027, filed on Jul. 9, 2013.

(51) Int. Cl.
*A61M 15/00* (2006.01)
*A61M 16/00* (2006.01)
(Continued)

(52) U.S. Cl.
CPC ...... *A61M 15/0085* (2013.01); *A61M 11/005* (2013.01); *A61M 15/00* (2013.01);
(Continued)

(58) Field of Classification Search
CPC ...... A61M 15/00–011; A61M 15/0028; A61M 15/0065–0078; A61M 15/009;
(Continued)

(56) References Cited

U.S. PATENT DOCUMENTS 6,192,876 B1 * 2/2001 Denyer ............... A61B 5/087
128/204.18
6,546,927 B2    4/2003 Behzadlan et al.
(Continued)

FOREIGN PATENT DOCUMENTS

CN    202289114 U    7/2012
CN    102695535 A    9/2012

*Primary Examiner* — Samchuan C Yao
*Assistant Examiner* — Ned T Heffner
(74) *Attorney, Agent, or Firm* — Daniel H. Brean

(57) ABSTRACT

Systems and methods for delivering medicament to a subject use one or more sensors to generate signals that represent characteristics of the ultrasonic energy emitted by a respiratory medicament delivery device during operation. Parameters based on these signals indicate energy amplitude in one or more frequency ranges. Such parameters can be used to control and/or monitor device operation and/or patient adherence.

10 Claims, 16 Drawing Sheets

(51) Int. Cl.
*A61M 16/20* (2006.01)
*A61M 11/00* (2006.01)
*A61M 16/14* (2006.01)

(52) U.S. Cl.
CPC ........ *A61M 15/001* (2014.02); *A61M 15/009* (2013.01); *A61M 16/0003* (2014.02); *A61M 16/14* (2013.01); *A61M 16/204* (2014.02); *A61M 2202/064* (2013.01); *A61M 2205/3375* (2013.01)

(58) Field of Classification Search
CPC .. A61M 15/0093; A61M 15/06; A61M 15/08; A61M 15/085; A61M 11/00; A61M 11/001–008; A61M 11/02–08; A61M 13/00; A61M 2205/3345; A61M 2205/3375; A61M 2205/505; A61M 2205/52; A61M 2230/40
See application file for complete search history.

(56) References Cited

U.S. PATENT DOCUMENTS

| | | | |
|---|---|---|---|
| 9,352,107 B2 | 5/2016 | Von Hollen | |
| 2002/0020408 A1* | 2/2002 | Knauer | A61M 15/0065 128/200.14 |
| 2010/0282247 A1 | 11/2010 | Fink et al. | |
| 2011/0226237 A1 | 9/2011 | Morrison | |
| 2012/0055472 A1 | 3/2012 | Brunnberg | |
| 2012/0312302 A1* | 12/2012 | Cardelius | A61M 16/104 128/203.14 |
| 2013/0151162 A1 | 6/2013 | Harris | |

* cited by examiner

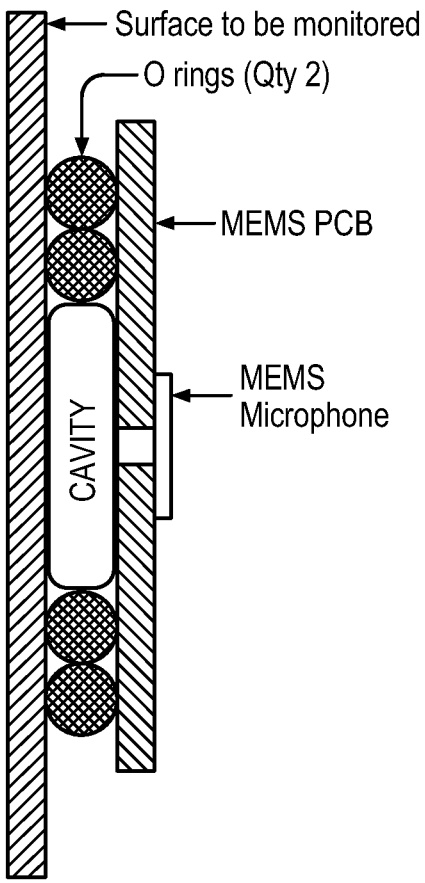 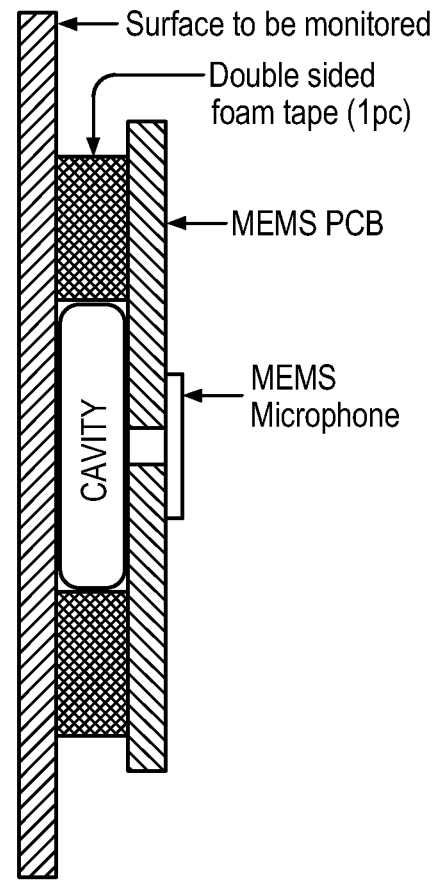
FIG. 15A          FIG. 15B
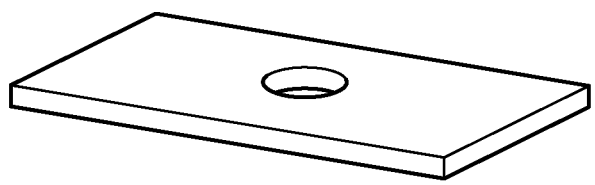
FIG. 15C
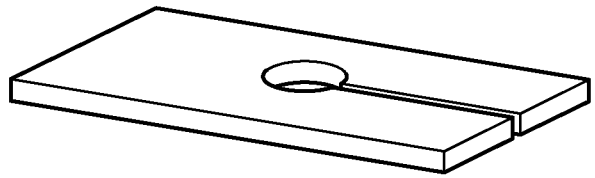
FIG. 15D

ULTRASONIC ENERGY MEASUREMENTS IN RESPIRATORY DRUG DELIVERY DEVICES

CROSS-REFERENCE TO RELATED APPLICATIONS

This patent application claims the priority benefit under 35 U.S.C. § 371 of international patent application no. PCT/IB2014/062449, filed Jun. 19, 2014, which claims the priority benefit under 35 U.S.C. § 119(e) of U.S. Provisional Application No. 61/844,027 filed on Jul. 9, 2013, the contents of which are herein incorporated by reference.

BACKGROUND

1. Field

The present disclosure pertains to systems and methods that measure ultrasonic energy in respiratory drug delivery devices, and, in particular, to control and/or monitor device operation and/or patient adherence based thereon.

2. Description of the Related Art

Respiratory drug delivery devices are used to treat many types of patients. Some types of respiratory drug delivery devices, for example nebulizers, include components that move at frequencies in the ultrasonic range. Device performance may depend on controlling such components with sufficient accuracy and efficacy. Positive treatment outcomes may depend on many factors, include patient adherence.

SUMMARY

Accordingly, one or more embodiments provide a system configured to deliver medicament to a subject. The system comprises a respiratory medicament delivery device, a sensor, and one or more processors configured to execute computer program modules, the computer program modules. The respiratory medicament delivery device is configured to combine breathable gas and medicament for delivery to an airway of a subject. The respiratory medicament delivery device emits ultrasonic energy during operation. The sensor is configured to generate output signals representing one or more characteristics of the ultrasonic energy emitted by the respiratory medicament delivery device during operation. The computer program modules comprise a parameter determination module, and/or other modules. The parameter determination module is configured to determine, based on the generated output signals, a first spectral parameter that indicates energy amplitude of the ultrasonic energy emitted by the respiratory medicament delivery device during operation in a first ultrasonic frequency range. The first spectral parameter characterizes operation of the respiratory medicament delivery device.

It is yet another aspect of one or more embodiments to provide a method of delivering medicament to a subject. The method comprises combining, by a respiratory medicament delivery device that emits ultrasonic energy during operation, breathable gas and medicament for delivery to an airway of a subject; generating, by a sensor, output signals representing one or more characteristics of the ultrasonic energy emitted by the respiratory medicament delivery device; and determining a first spectral parameter that indicates energy amplitude of the ultrasonic energy emitted by the respiratory medicament delivery device during operation, wherein the ultrasonic energy is emitted in a first ultrasonic frequency range, and wherein the first spectral parameter characterizes operation of the respiratory medicament delivery device.

It is yet another aspect of one or more embodiments to provide a system configured to deliver medicament to a subject. The system comprises means for combining breathable gas and medicament for delivery to an airway of a subject, wherein the means for combining emits ultrasonic energy during operation; means for generating output signals representing one or more characteristics of the ultrasonic energy emitted by the means for combining; and means for determining a first spectral parameter that indicates energy amplitude of the emitted ultrasonic energy, wherein the ultrasonic energy is emitted in a first ultrasonic frequency range, and wherein the first spectral parameter characterizes operation of the means for combining.

These and other aspects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of any limits.

BRIEF DESCRIPTION OF THE DRAWINGS

FIGS. 15A-15D illustrate various implementations to accomplish energy measurements from a surface on or within respiratory medicament delivery devices.

DETAILED DESCRIPTION OF EXEMPLARY EMBODIMENTS

Figure 1:
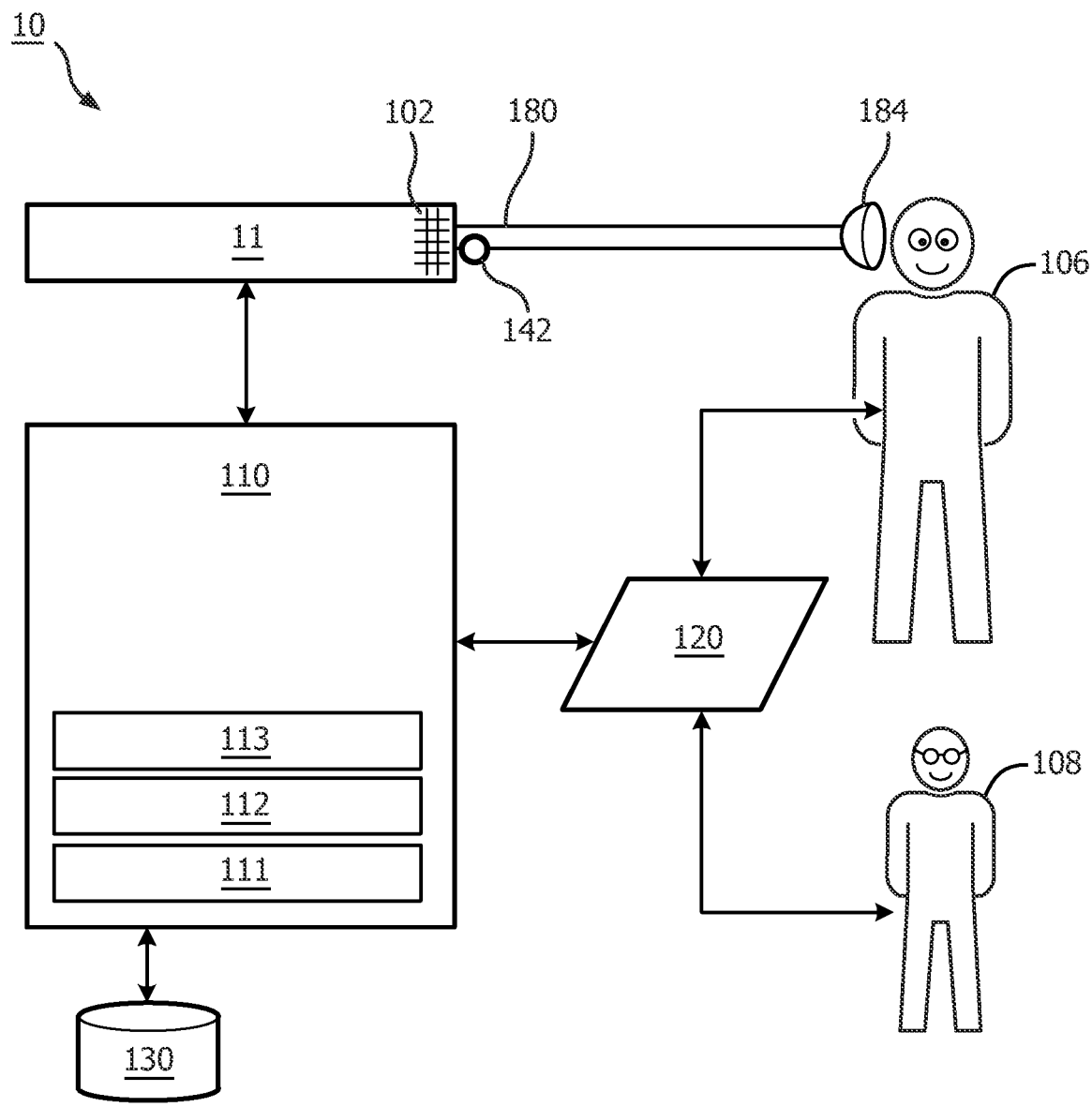
FIGS. 1, 12-14 schematically illustrate systems configured to deliver medicament to a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 10 configured to deliver medicament to a subject 106. System 10 may include one or more of a respiratory medicament delivery device 11, an inhalation flap valve 12, one or more sensors 142, one or more processors 110, a parameter determination module 111, a control module 112, an adherence module 113, an electronic storage 130, a user interface 120, and/or other components and/or computer program modules.

Respiratory medicament delivery device 11 may be one or more of a jet nebulizer, a mesh nebulizer, an ultrasonic wave nebulizer, a nebulizer, an aerosol generator, a metered-dose inhaler, a dry-powder inhaler, an inhaler, and/or another device configured to deliver medicament to a subject through, at least in part, respiration of the subject. In some implementations, respiratory medicament delivery device 11 may include one or more features of any of these devices. Respiratory medicament delivery device 11 may be configured to combine breathable gas, e.g. air, and medicament, e.g. liquid and/or aerosolized drugs, for delivery to the airway of subject 106. Respiratory medicament delivery device 11 may emit energy during operation, including, but not limited to, ultrasonic energy. Respiratory medicament delivery device 11 may be configured such that a constituent component of respiratory medicament delivery device 11 displaces air and/or gas through mechanical movement at an ultrasonic frequency. Such displacement may be indirect, e.g. when a moving component is coupled to another component which transfers energy to air and/or gas. In some implementations, respiratory medicament delivery device 11 may emit energy in a frequency range between about 18 kHz and about 200 kHz, and/or any sub-range thereof. The specific frequency range may depend on the type of respiratory medicament delivery device that is used. In some implementations, respiratory medicament delivery device 11 may be operated by care provider 108, e.g. a medical professional. In some implementations, respiratory medicament delivery device 11 may include a conduit 180 to guide gas and/or medicament to subject 106 and/or a mouthpiece 184 to deliver gas and/or medicament from conduit 180 to the airway of subject 106.

In some implementations, respiratory medicament delivery device 11 may include a mesh nebulizer and/or components/features thereof. In some implementations, respiratory medicament delivery device 11 may include an ultrasonic wave nebulizer and/or components/features thereof. In some implementations, respiratory medicament delivery device 11 may include an aerosol generator and/or components/features thereof. Mesh nebulizers, ultrasonic wave nebulizers, and/or aerosol generators may include a piezoelectric element to provide mechanical vibration and thus displacement of a medium, e.g. liquid or air. Nebulizers filled with liquid may include moving components that transfer ultrasonic energy to air and/or gas. In some implementations, one or more other surfaces in direct contact with air and/or gas may move as a result of the motion of, e.g., a piezoelectric element. Any vibrating surface may emit ultrasonic energy. For example, the backside of a piezoelectric element may contact (and/or be coupled with) air and/or gas. In some implementations, the piezoelectric element is coupled with a mesh (e.g. a mesh nebulizer) having a side that is directly (or indirectly) in contact with air and/or gas. In some implementations, a static mesh may be placed at some harmonic distance from a vibrating piezoelectric element.

Such piezoelectric elements may achieve maximum displacement at one or more particular frequencies, referred to as resonant frequencies. Maximum displacement may be targeted as a preferred mode of operation (and/or the operating frequency). The operating frequency may characterize operation of the piezoelectric element and/or respiratory medicament delivery device 11. Operating conditions and/or maximum displacement may change over time, e.g. depending on the amount of available medicament within the device, the loading, drift of an oscillator used with/within the device, wear and tear of the device, ambient operating conditions such as temperature, humidity, atmospheric pressure, air density, and/or other factors that may change over time. Operating conditions and/or maximum displacement may differ between individual devices, e.g. based on construction, assembly, and/or other device-specific conditions. The particular operating condition having maximum displacement may be assumed to coincide, or at least be close to, the operating condition in which respiratory medicament delivery device 11 emits a maximum amount of ultrasonic energy. As used herein, the term "maximum" may refer to a local maximum in a specific range of operation.

By virtue of this disclosure, operating conditions for respiratory medicament delivery device 11 may be controlled and/or adjusted to track changes in (maximum) displacement, operating conditions, target frequencies similar and/or close to resonant frequencies, and/or monitor device usage (e.g. as indicative of patient adherence), and/or other changes. Control and/or adjustment may be based on (feedback of) measurements of ultrasonic energy emitted by respiratory medicament delivery device 11. In some implementations, adjustments may be made in real-time or near-real-time. In some implementations, adjustments may be made automatically, autonomously, and/or without manual user intervention. In some implementations, respiratory medicament delivery device 11 may include an electronic oscillator or similar device/component to control the driving frequency of the piezoelectric element and/or other component configured for intentional displacement of, e.g., a medium.

Figure 9:
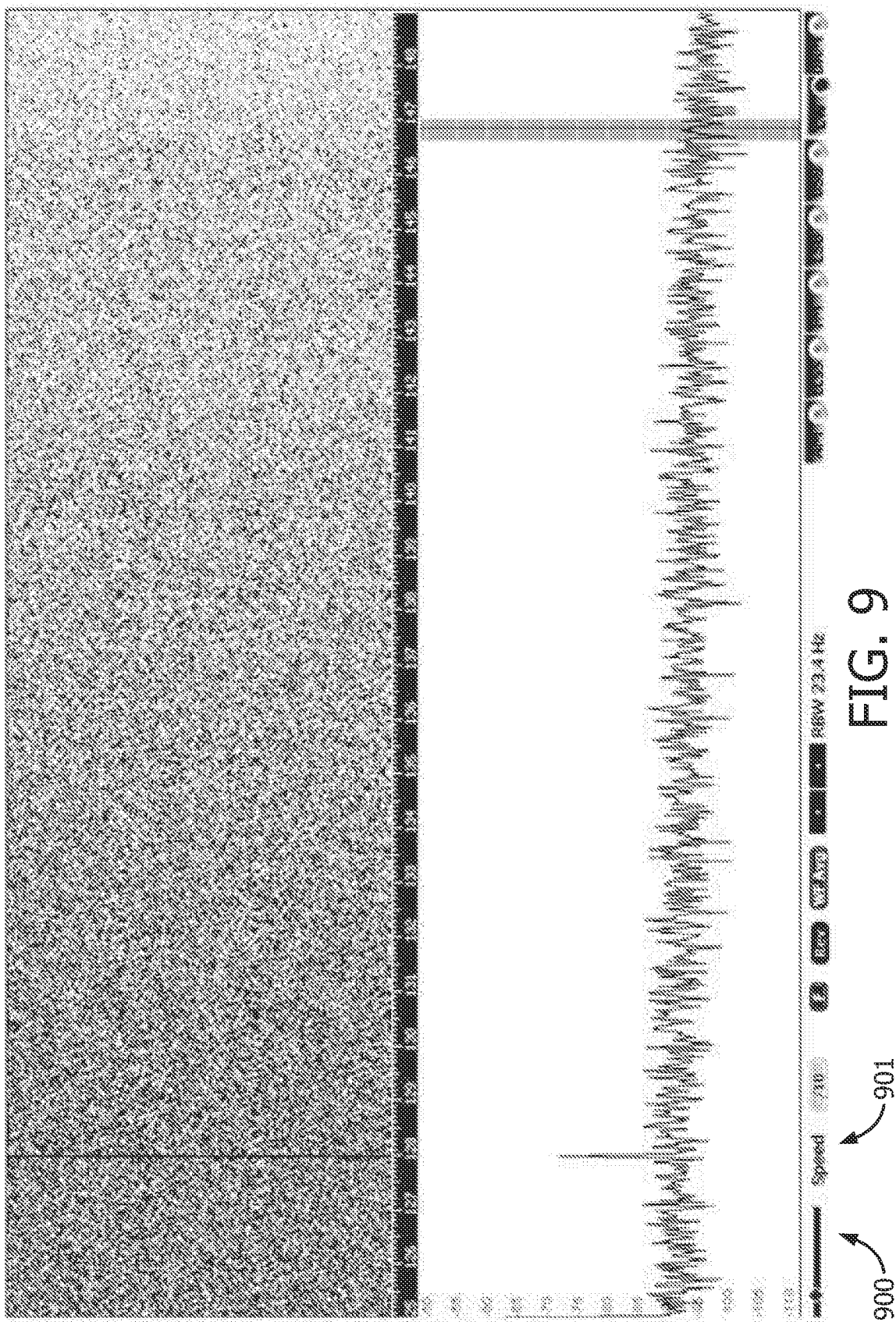

By way of illustration, FIG. 9 illustrates a graph 900 for energy emitted during the operation of a mesh nebulizer. Graph 900 includes a waterfall display in the top half, and a magnitude (of energy amplitude) in the bottom half. The waterfall display shows time on the vertical axis and measured frequency (in kHz) in the horizontal axis. As depicted in FIG. 9, graph 900 includes a narrow peak magnitude near a frequency of 128 kHz, which is the operating frequency for the piezoelectric element in the mesh nebulizer. Referring to FIG. 1, energy may be measured using one or more sensors 142. As used herein, the term "magnitude" may be used to refer to the energy amplitude at a particular frequency and/or within a particular range of frequencies.

One or more sensors 142 of system 10 in FIG. 1 are configured to generate output signals representing one or more characteristics of ultrasonic energy emitted by respiratory medicament delivery device 11. In some implementations, sensor 142 may include a microphone (referred to as microphone 142). For example, sensor 142 may include a microphone constructed as a micro-electro-mechanical system (MEMS) or nano-electro-mechanical system (NEMS). As used herein, the term "MEMS" may be used to refer to either MEMS or NEMS. As used in this disclosure, the term "microphone" may be used to refer to a MEMS microphone, and may be used for audible and/or ultrasonic frequencies/sounds.

The one or more sensors 142 may include an accelerometer, positional sensor, movement sensor, light sensor, infrared (IR) sensor, electromagnetic sensor, electrode, tilt meter, (video) camera, and/or other sensors. The illustration of sensor 142 including one member in FIG. 1 is not intended to be limiting. In some embodiments, system 10 may use multiple sensors. The illustration of the location of sensor 142 as depicted in FIG. 1 is not intended to be limiting. An individual sensor 142 may be located at or near (a body part of) subject 106, embedded and/or integrated in respiratory medicament delivery device 11, and/or at other locations. Resulting output signals or conveyed information from one or more sensors 142 may be transmitted to processor 110, user interface 120, electronic storage 130, and/or other components of system 10. Transmission may be wired and/or wireless.

The one or more sensors 142 may be configured to generate output signals in an ongoing manner, e.g. before, during, and/or after delivery of medicament. This may include generating signals intermittently, periodically (e.g. at a sampling rate), continuously, continually, at varying intervals, and/or in other ways that are ongoing. The sampling rate may be about $10^{-9}$ second, about $10^{-8}$ second, about $10^{-7}$ second, $10^{-6}$ second, $10^{-5}$ second, $10^4$ second, 0.001 second, 0.01 second, 0.1 second, 1 second, about 10 seconds, about 1 minute, and/or other sampling rates. It is noted that multiple individual sensors 142 may operate using different sampling rates, as appropriate for the particular output signals and/or (frequencies related to particular) parameters and/or characteristics derived therefrom. For example, in some embodiments, the generated output signals may be considered as a vector of output signals, such that a vector includes multiple samples of information conveyed related to one or more parameters and/or characteristics. A particular parameter or characteristic determined in an ongoing manner from a vector of output signals may be considered as a vector of that particular parameter or characteristic.

In some implementations, sensor 142 may be a MEMS microphone configured and/or arranged to measure ultrasonic energy transferred from any flat and/or curved surface within respiratory medicament delivery device 11 and/or any such exterior surface of respiratory medicament delivery device 11. By way of illustration, FIGS. 15A-15D illustrate various implementations to accomplish energy measurements from surfaces. FIG. 15A illustrates that a cavity may be created between the surface to be monitored and the printed circuit board (PCB) onto which the MEMS microphone is mounted. The cavity may be filled with air and/or gas. As depicted in FIG. 15A, the cavity may be enclosed by two o-rings. In an alternate implementation, depicted in FIG. 15B, the cavity may be formed within a piece of tape, for example double-sided foam tape. Such a piece of tape is shown separately, from an isometric view, in FIG. 15C. In some implementations, measurements may be improved and/or have improved sensitivity in a particular direction by cutting a channel in the tape. Such an implementation is shown in FIG. 15D.

In some implementations, sensor 142 may be configured to generate output signals conveying measurements related to gas parameters of respiratory airflow, parameters related to airway mechanics, and/or other parameters. Gas parameters may include flow, (airway) pressure, humidity, velocity, acceleration, and/or other gas parameters. Output signals may convey measurements related to respiratory parameters. Sensor 142 may be in fluid communication with conduit 180 and/or mouthpiece 184. Sensor 142 may generate output signals related to physiological parameters pertaining to subject 106. Parameters may be associated with the state and/or condition of an airway of subject 106, the breathing of subject 106, the gas breathed by subject 106, the composition of the gas breathed by subject 106, the delivery of the gas to the airway of subject 106, and/or a respiratory effort by the subject.

Figure 10:
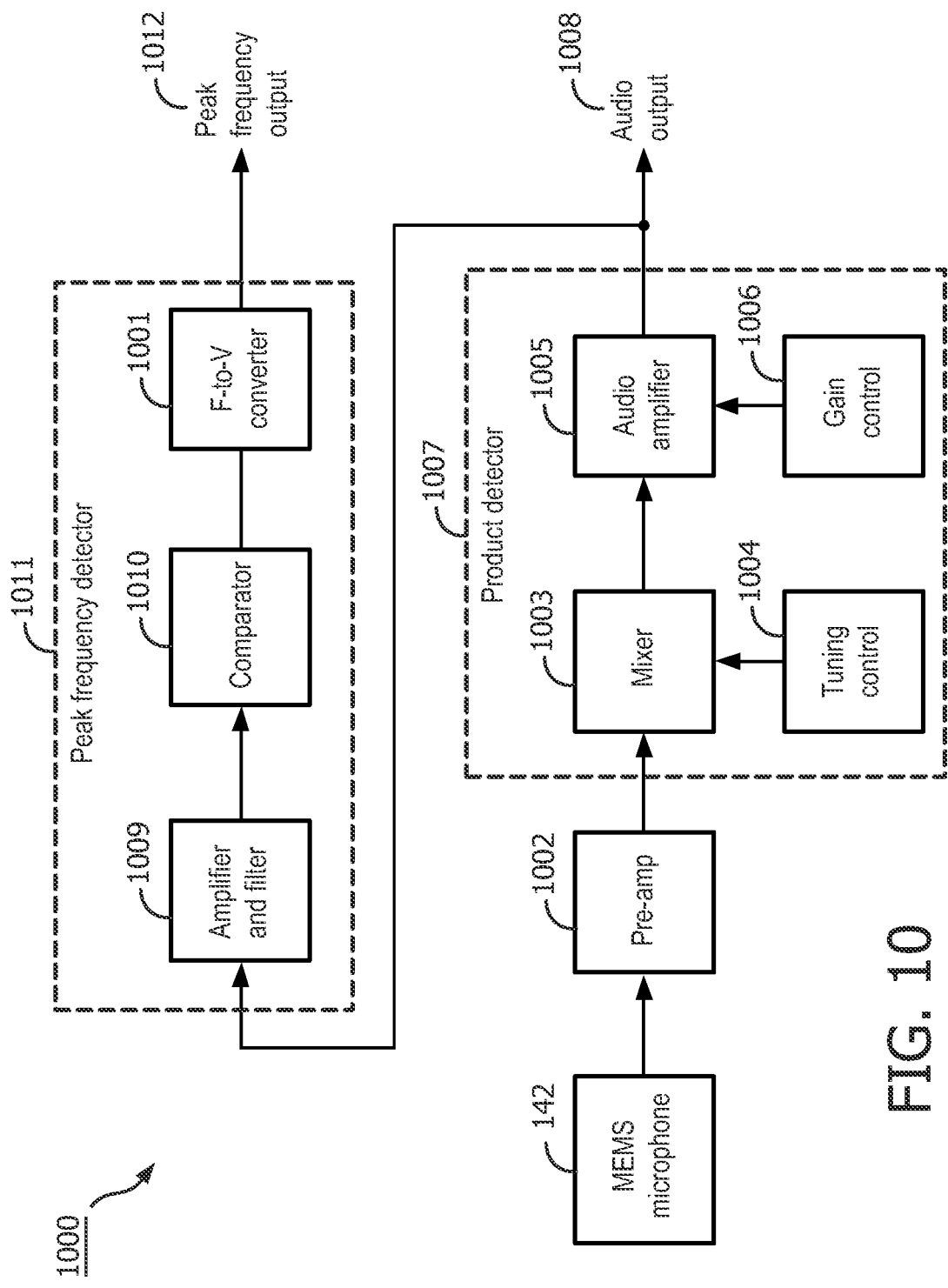
FIG. 10-11 illustrate subsystems for processing signals representing received ultrasonic energy as may be used in a system configured to deliver medicament to a subject.
Figure 11:
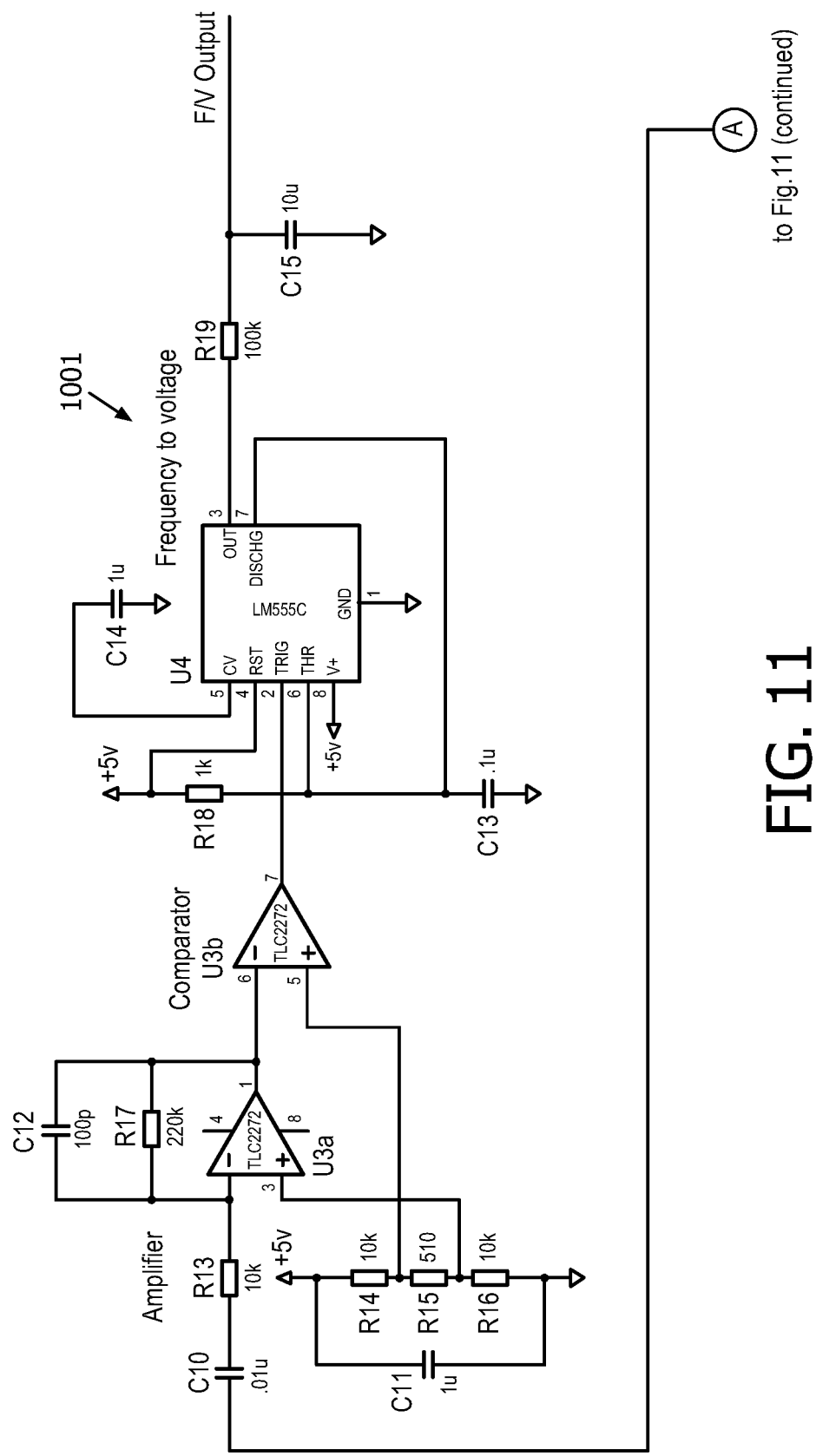
Figure 11:
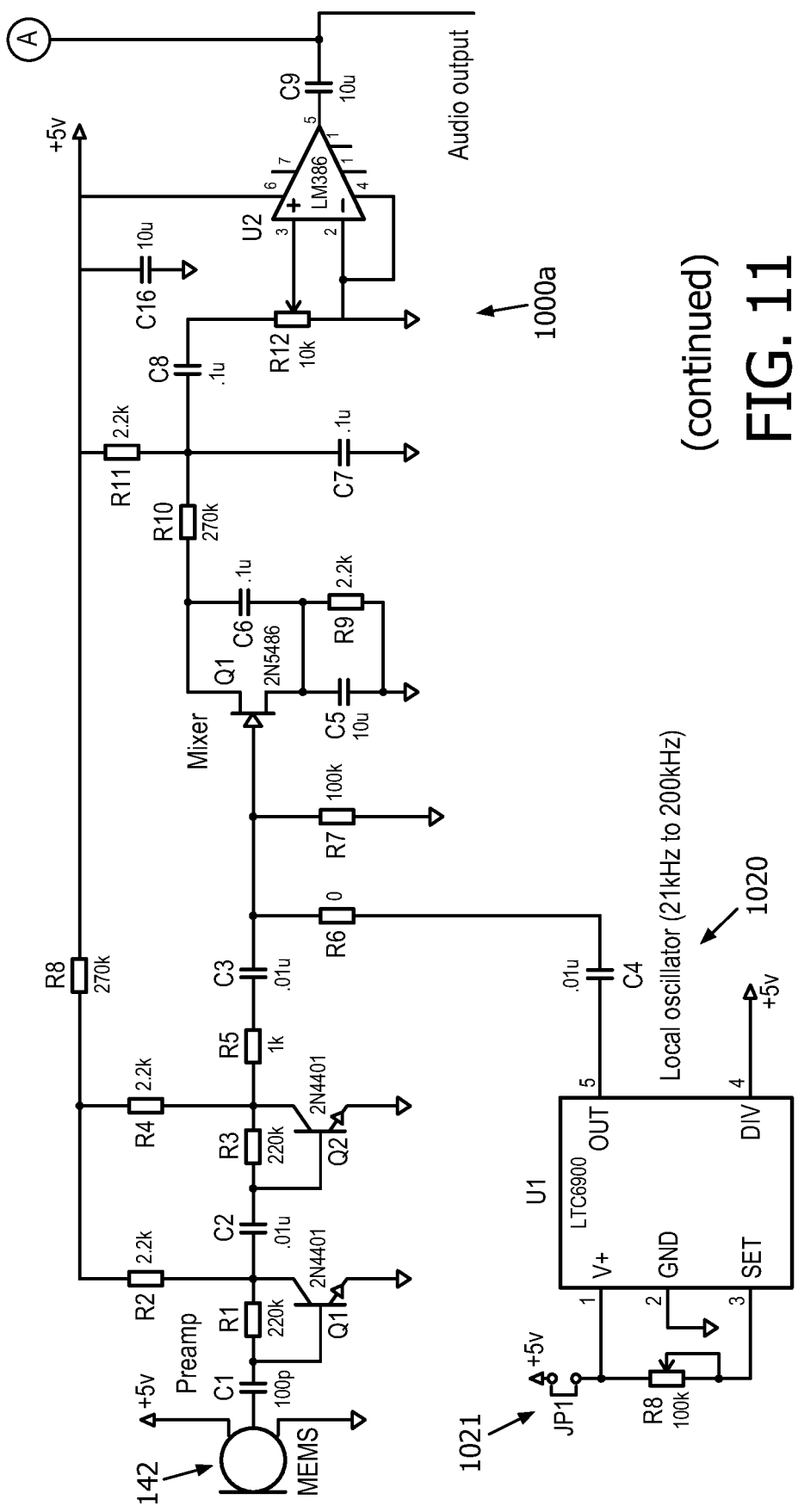

By way of illustration, FIGS. 10 and 11 schematically illustrate various components forming subsystems 1000 and 1000a, respectively. Subsystems 1000 and 1000a may a frequency-to-voltage circuit 1001. Subsystems 1000 and 1000a may represent similar features and functionality. Subsystem 1000, subsystem 1000a, and/or components thereof may be included and/or used in embodiments of system 10 (FIG. 1). Acoustic and/or ultrasonic energy (including energy emitted by respiratory medicament delivery device 11) may be received and/or measured by microphone 142. A pre-amplifier 1002 may be configured to include a high pass filter and/or a coupling capacitor. Pre-amplifier 1002 may be used before the incoming signal is amplified, for example as depicted in FIG. 11 by using two transistors. A product detector 1007 may be configured to detect the type of respiratory medicament delivery device is in operation, based on the measured ultrasonic energy. Product detector 1007 may include mixer 1003, tuning control 1004, audio amplifier 1005, gain control 1006, and/or other components. Mixer 1003 may include a transistor driven by both pre-amplifier 1002 and (as depicted in FIG. 11) a local oscillator 1020. Mixer 1003 may be configured to multiply its two inputs with the resulting output, thus producing sum and difference frequencies. Audio amplifier 1005 may be configured to amplify the signal created by mixer 1003 and/or to provide a comfortable listening level for a user listening to audio output 1008. Gain control may be configured to control gain for audio amplifier 1005. Output from audio amplifier 1005 may be transmitted to peak frequency detector 1011. Peak frequency detector 1011 may include an amp-and-filter 1009, a comparator 1010, a frequency-to-voltage circuit 1001, and/or other components. Peak frequency detector 1011 may be configured to generate a (direct current) output voltage that is proportional to the (dominant) frequency as received through microphone 142. Amp-and-filter 1009 may provide additional amplification and filtering of the signal prior to comparator 1010 digitizing it. The resulting pulse train may be used to trigger a pulse entering a capacitor, thus adding charge to the capacitor. The charge on the capacitor may represent the (dominant) frequency as received through microphone 142. Alternatively, and/or simultaneously, such a pulse train may be used to increment a timer and/or counter, to be used in a similar manner as the capacitor.

In some implementations, subsystems the same as or similar to subsystems 1000 and 1000a may be used as narrow-band special-purpose microphones. For example, the emitted ultrasonic energy for mesh nebulizers and dry-powder inhalers may be a narrow-band signal for which subsystems 1000 and 1000a as depicted may be suitable.

Figure 6:
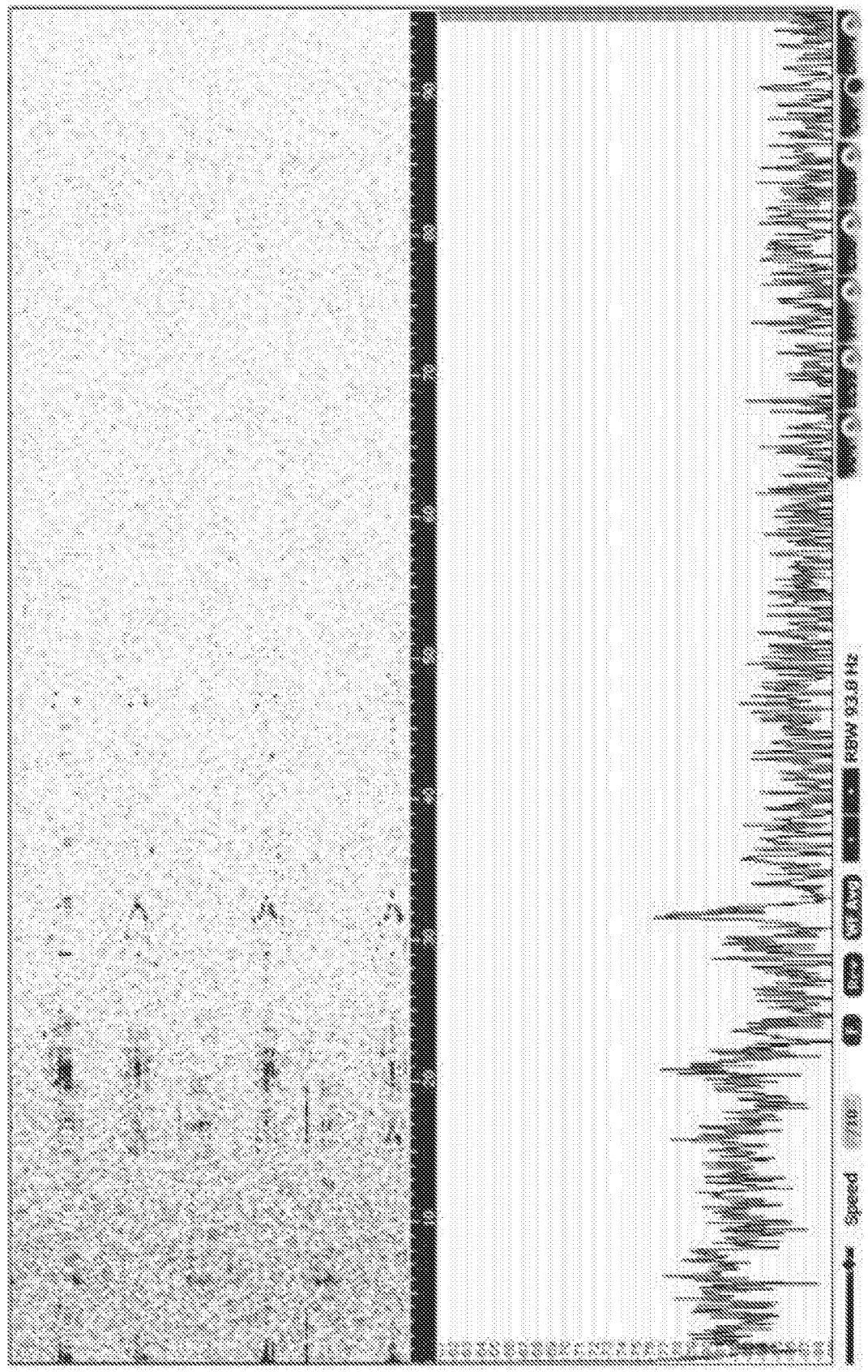
Figure 7:
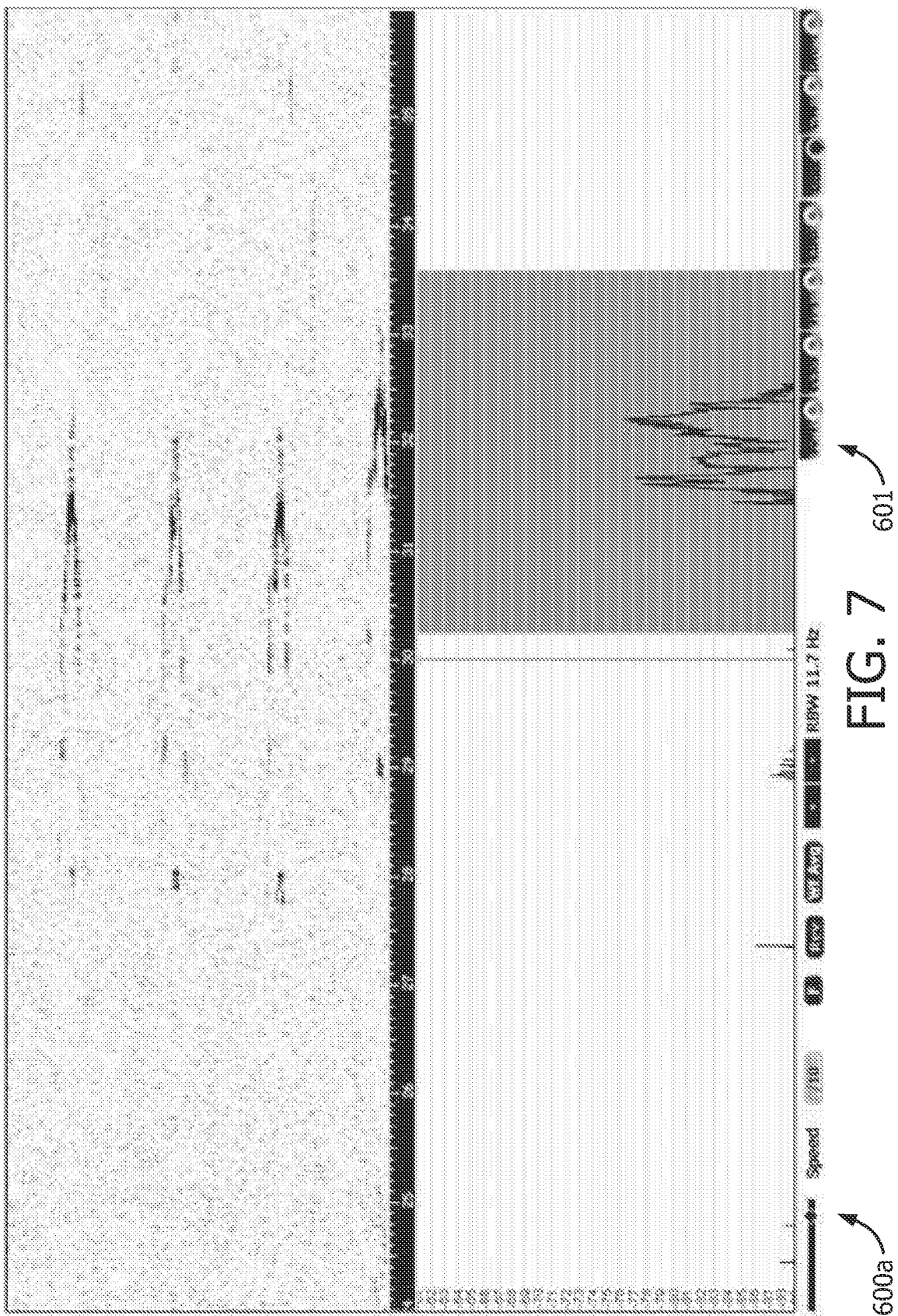
Figure 8:
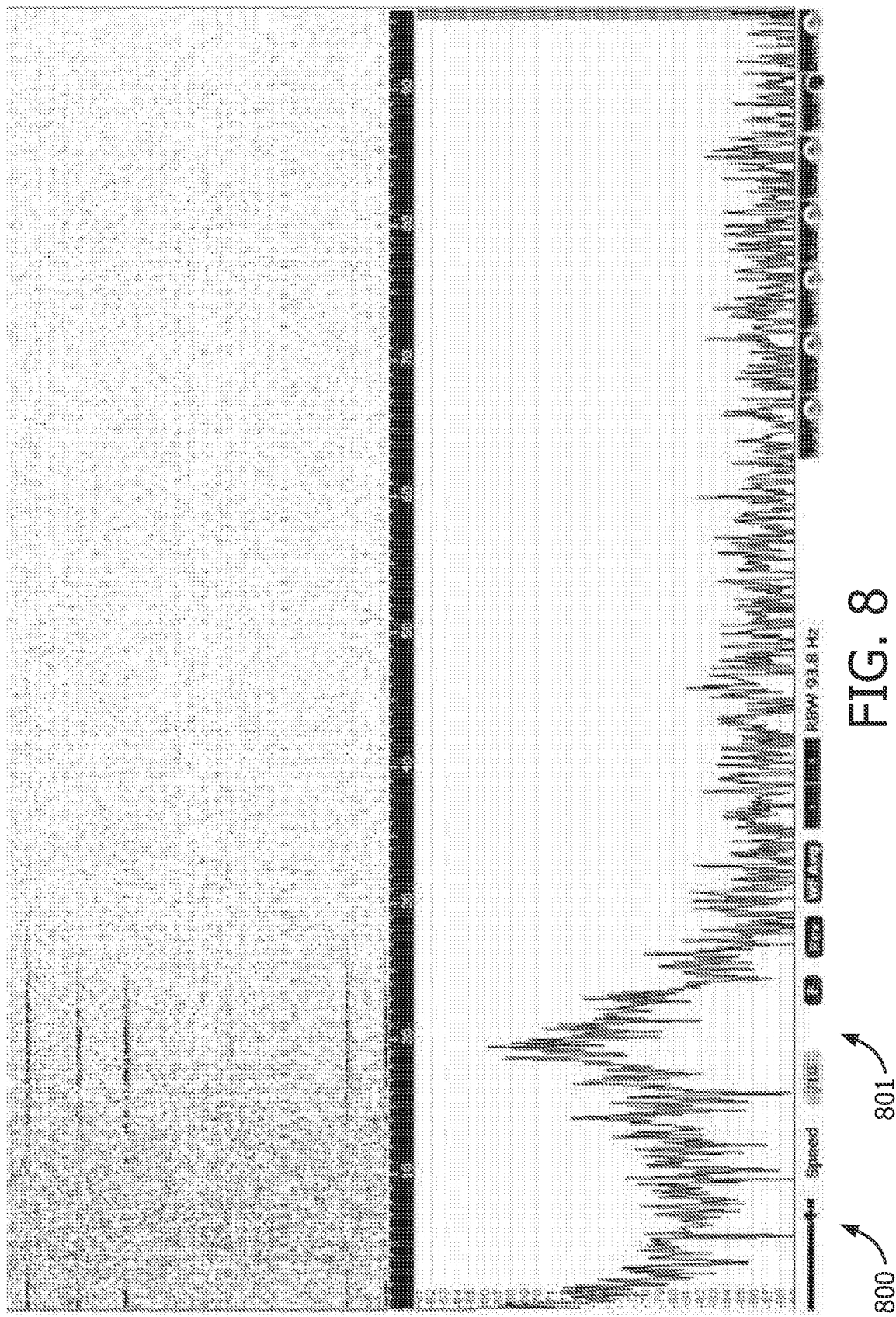

By way of illustration, FIGS. 6 and 7 illustrate graphs 600 and 600a for energy emitted during the operation of a dry-powder inhaler. Graphs 600 and 600a include a waterfall display in the top half, and a magnitude (of energy amplitude) in the bottom half. The waterfall display shows time on the vertical axis and measured frequency (in kHz) in the horizontal axis. As depicted in FIG. 6, graph 600 includes a narrow peak magnitude 601 near a frequency of 31 kHz, which may be an ultrasonic energy signature for the delivery of medicament through the dry-powder inhaler. This energy may be emitted as air rushes past a drug capsule and/or by resonance within respiratory medicament delivery device 11 during operation. The top half of graph 600 depicts three distinct ultrasonic whistles that each begin at about 31 kHz, increase smoothly to about 33 kHz, and then return smoothly to about 31 kHz. FIG. 7 illustrates a magnified view of FIG. 6.

Figure 12:
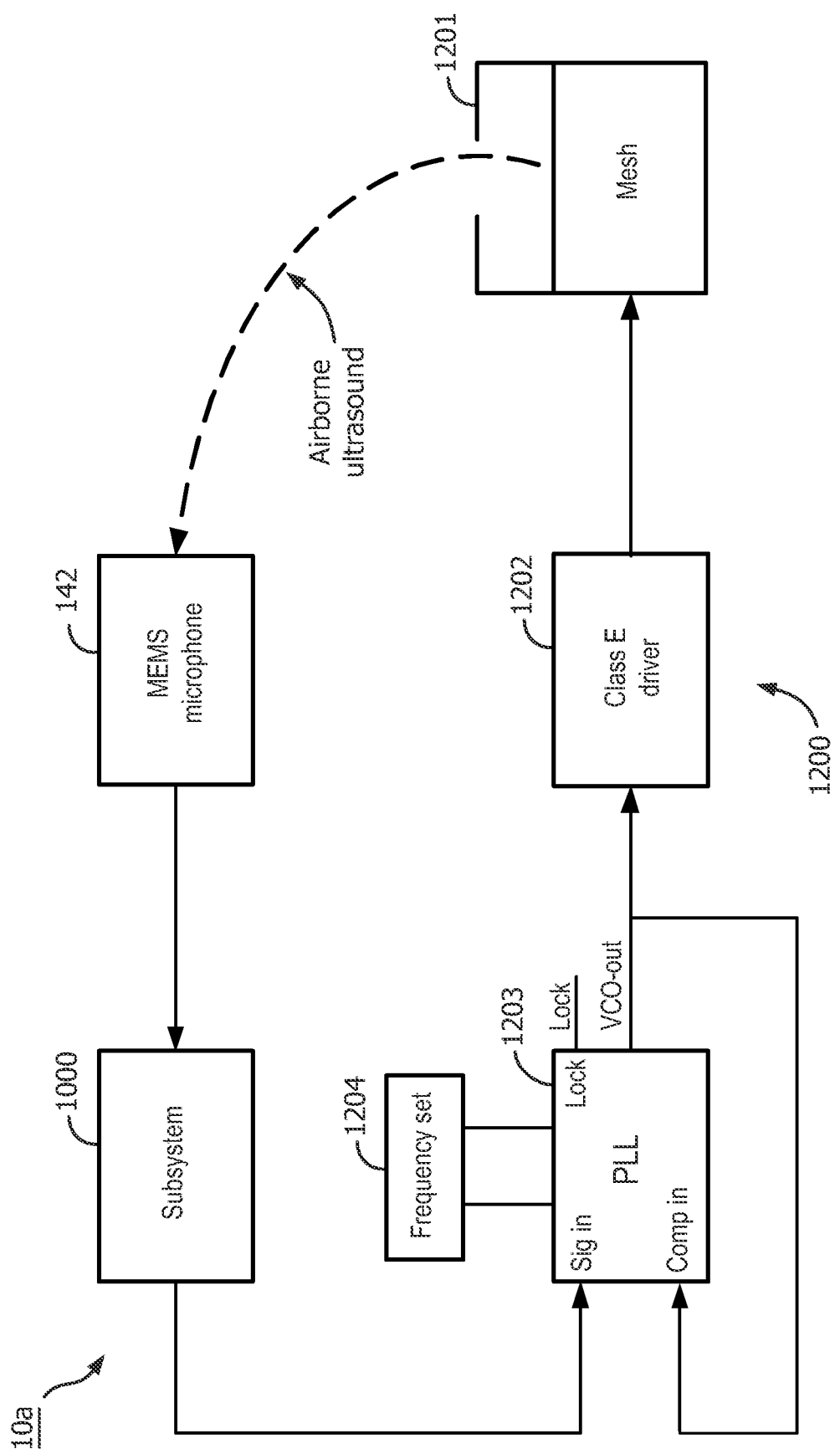

Referring to FIGS. 10 and 11, subsystems the same as or similar to subsystems 1000 and 1000a may be used in a larger system configured to deliver medicament to a subject, such as system 10 (FIG. 1) and/or systems similar to system 10. By way of illustration, FIG. 12 schematically illustrates a system 10a that includes a mesh nebulizer 1200, microphone 142, subsystem 1000, and/or other components. Mesh nebulizer 1200 may include a mesh 1201, a class E driver 1202, a phase-locked loop circuit (PLL) 1203, and/or other components. PLL 1203 may include inputs "signal in" and "comparator in," and outputs "VCO-out" and "lock," all of which are standard for PLLs. Note that output VCO-out loops back to input "comparator in." PLL 1203 may be configured to provide a driving frequency for mesh 1201 (through a suitable driver such as Class E driver 1202) and/or a piezoelectric element connected to mesh 1201. In some implementations, PLL 1203 may be configured to adjust the driving frequency based on a phase difference between the ultrasonic energy measured through microphone 142 and the signal/frequency used to drive mesh 1201 (e.g. from output VCO-out). Note that microphone 142 may need to be positioned such that contact with aerosol is avoided or minimized, e.g. by placing microphone 142 at a suitable harmonic distance (i.e. one or more cycles) from mesh 1201. Note that the signal from output VCO-out may be a square wave, whereas the signal from mesh 1201 may be a sinusoid, though their frequencies are necessarily the same.

If and/or when the operating frequency of mesh 1201 changes away from resonance, the energy emitted by mesh 1201 will decrease in amplitude (due to the impedance curve of the element used to drive mesh 1201), effectively increasing the phase difference. In response, PLL 1203 may adjust its output frequency to counteract this condition. Contrary to respiratory medicament delivery devices that are intentionally driven at a frequency other than their resonance frequency (e.g. to avoid frequency adjustments on the opposite side of the impedance curve), the systems disclosed herein may operate much closer to the resonance frequency, e.g. letting PLL 1203 track changes in operation based on the signals generated by microphone 142. In some implementations, mesh nebulizer 1200 may include a frequency set 1204 configured to manually and/or programmably control PLL 1203.

PLL 1203 may be configured, once it is locked, to adjust operating conditions such that the phase difference is minimized, and the energy amplitude (at least locally) maximized. The features described in this disclosure may be used to detect conditions including sputter, end of treatment, and/or other conditions.

Figure 3:
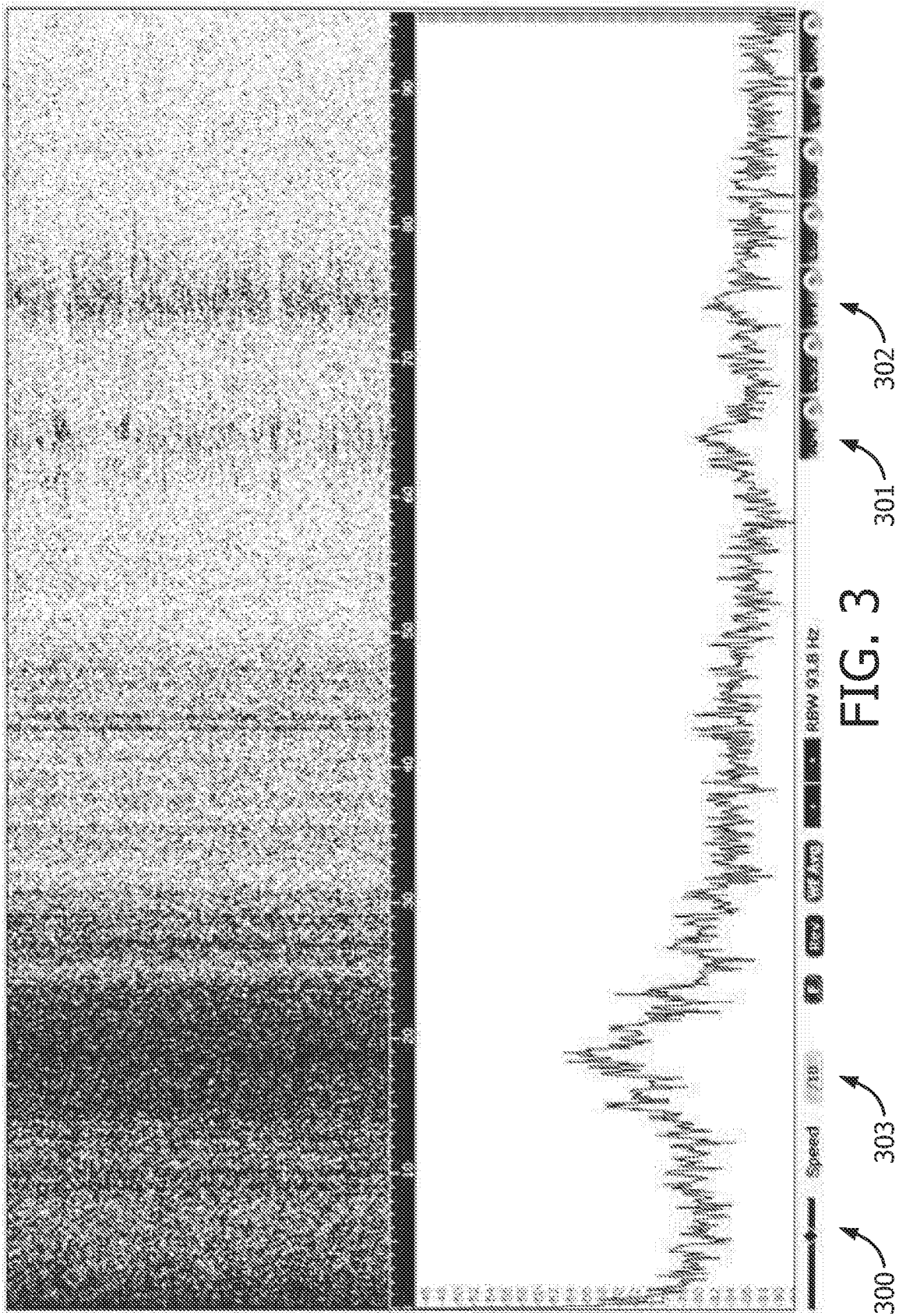
FIG. 3-9 illustrate graphs for energy emitted during the operation of various respiratory medicament delivery devices as may be used in a system configured to deliver medicament to a subject.
Figure 4:
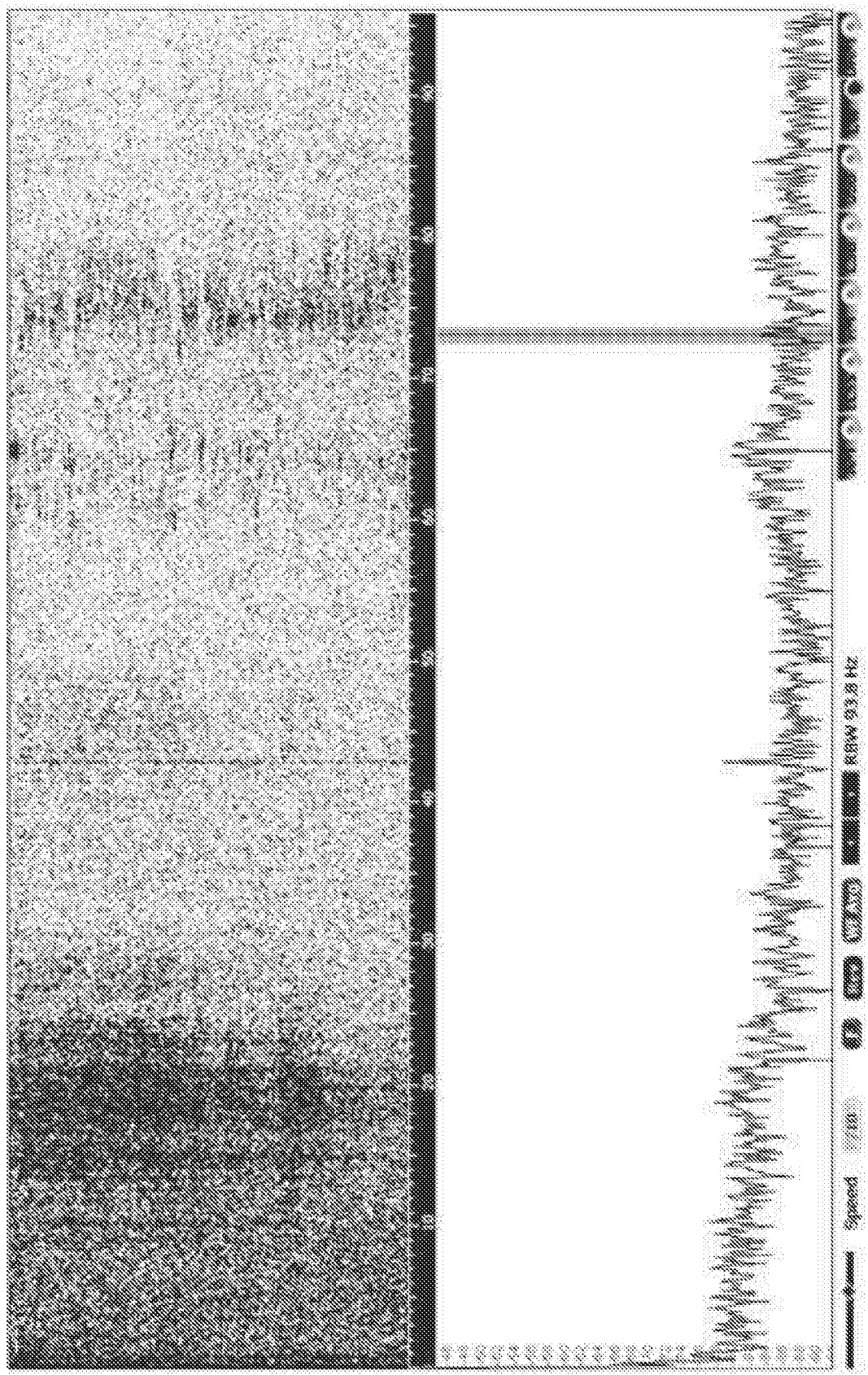

Referring to FIG. 1, in some implementations, respiratory medicament delivery device 11 may include a jet nebulizer and/or components/features thereof. Jet nebulizers may include compressed air. The emitted ultrasonic energy for jet nebulizers may be a wide-band signal. Such a signal may be measured using a subsystem such as subsystem 1000a in FIG. 11, but with jumper 1021 removed (and resistor R9 changed from 10 kOhm to 2 kOhm), and thereby not using product detector 1007 (FIG. 10) or local oscillator 1020 (FIG. 11). In this mode of operation, the subsystem may be suitable for wide-band signals between about 15 kHz and about 65 kHz. By way of illustration, FIGS. 3 and 4 illustrate graphs 300 and 300a for energy emitted during the operation of a jet nebulizer. Graphs 300 and 300a include a waterfall display in the top half, and a magnitude (of energy amplitude) in the bottom half. The waterfall display shows time on the vertical axis and measured frequency (in kHz) in the horizontal axis. As depicted in FIG. 3, graph 300 includes a wide band signal 303 between about 15 kHz and about 21 kHz, which appeared after liquid medicament was added to the jet nebulizer. Note that distinct peaks 301 and 302 in energy magnitude appear at about 64 kHz and 74 kHz, respectively. FIG. 4 illustrates operation of a jet nebulizer at the commencement of sputter. Information derived from graphs such as graphs 300 and 300a may be used to control operation of a respiratory medicament delivery device and/or monitor respiratory parameters (e.g. as indicative of patient adherence).

Figure 5:
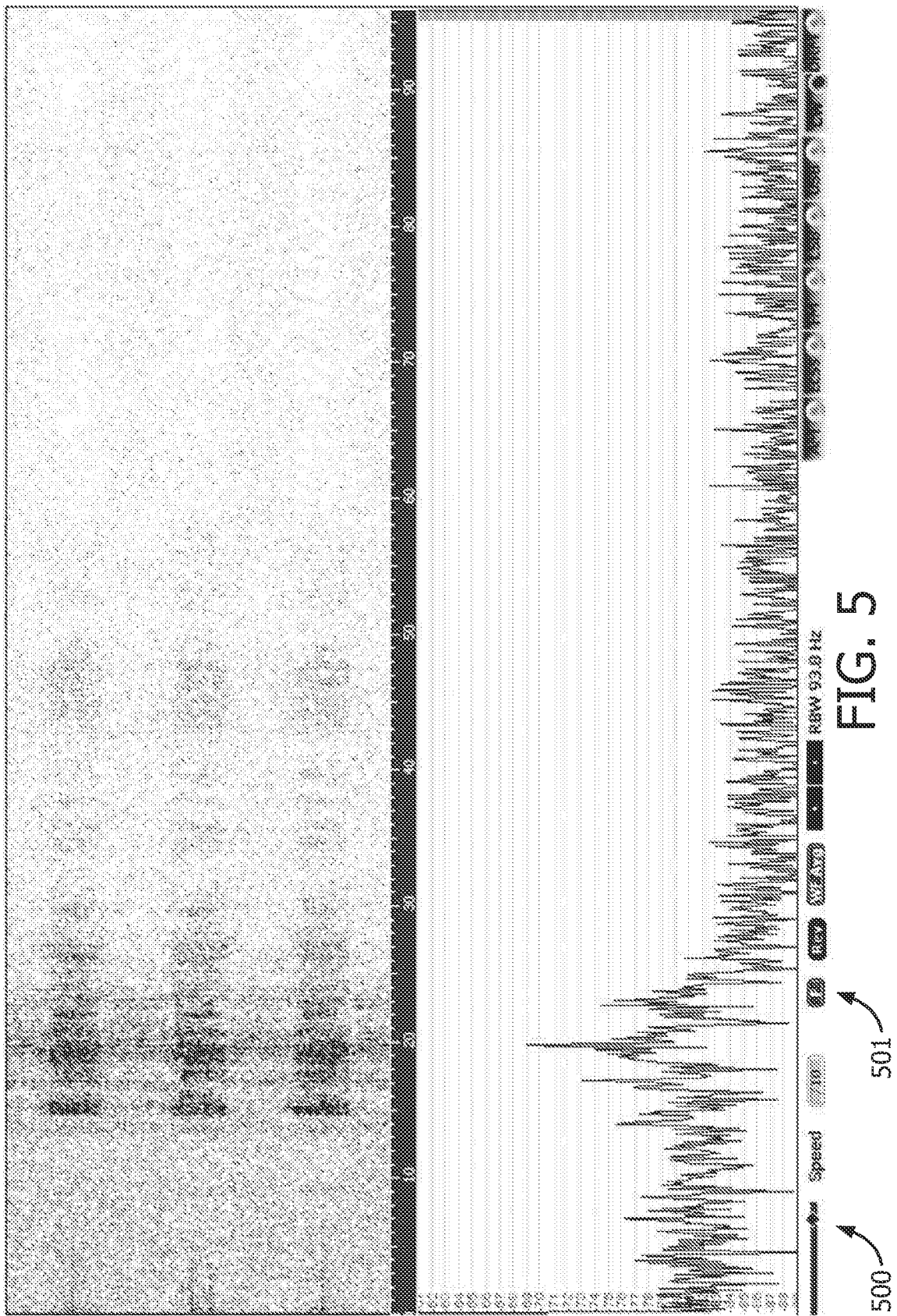
Figure 13:
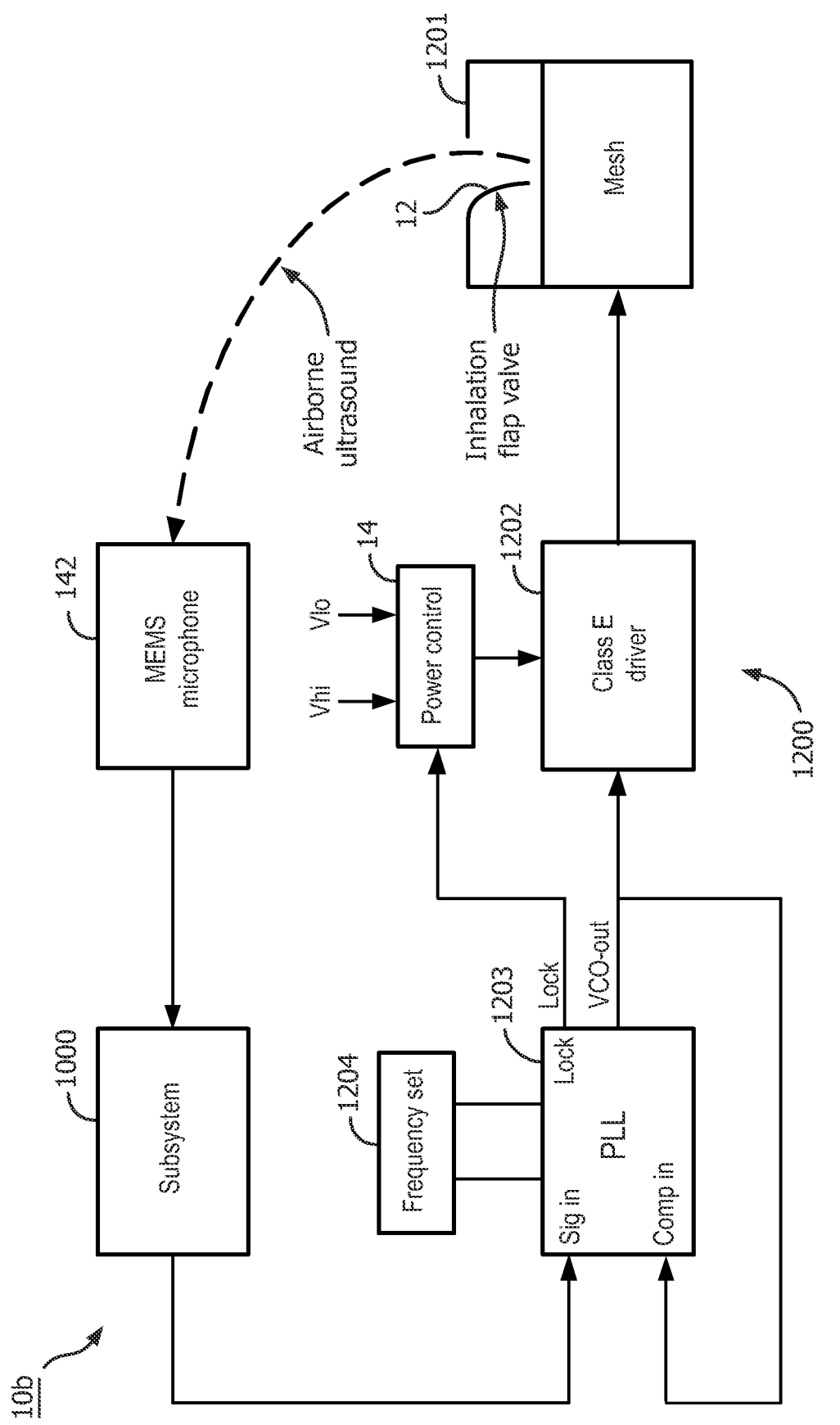

In some implementations, system 10 includes an inhalation flap valve 12. Inhalation flap valve 12 may be configured to move responsive to a flow of air and/or gas. Inhalation flap 12 valve may be included in a flow path of respiratory medicament delivery device 11. For example, inhalation flap valve 12 may be configured to move responsive to respiration by subject 106. For example, inhalation flap valve 12 may open responsive to inhalation by subject 106 and/or close responsive to exhalation by subject 106. Inhalation flap valve 12 may be configured and/or arranged to reduce the ultrasonic energy received by microphone 142. By way of illustration, FIG. 13 schematically illustrates a system 10b, similar to system 10a in FIG. 12, that includes an inhalation flap valve 12. By way of illustration, FIG. 5 illustrates a graph 500 for energy emitted during the operation of a nebulizer that includes an inhalation flap valve, e.g. as depicted in FIG. 13. Note the differences and similarities between graph 300 in FIG. 3 and graph 500 in FIG. 5.

Referring to FIG. 5, graph 500 includes a waterfall display in the top half, and a magnitude (of energy amplitude) in the bottom half. The waterfall display shows time on the vertical axis and measured frequency (in kHz) in the horizontal axis. As depicted, graph 500 includes a wide band signal 501 between about 15 kHz and about 21 kHz. Note the three distinct increases that coincide with inhalation flap valve 12 being open. Information derived from graphs such as graph 500 may be used to control operation of a respiratory medicament delivery device and/or monitor respiratory parameters (e.g. as indicative of patient adherence). For example, such information may be used to control delivery of medicament to subject 106. This may avoid wasting medicament during exhalation. Referring to FIG. 1, in some implementations, system 10 may be configured to adjust the operating frequency (e.g. off-resonance) and/or reduce (drive) power responsive to the inhalation flap valve being closed. As a result, aerosol production may be reduced and/or halted; at least until the inhalation flap valve is opened upon the next inhalation by subject 106. Such a mode of operation may be referred to as breath-actuated. Variations using an exhalation flap valve are considered within the scope of this disclosure.

Referring to FIG. 13, in some implementations, system 10b may include power control 14. Power control 14 may be controlled based on, at least in part, an output from PLL 1203, such as, e.g., the lock output. When PLL 1203 is locked, e.g. when inhalation flap valve 12 is open, power control 14 may be configured to control Class E driver 1202 to use a high power setting that is sufficient for system 10*b* to produce aerosol. When PLL 1203 is not locked, a low power setting may be used. Note that the low power setting may need to be sufficiently powerful such that, once inhalation flap valve 12 is opened again, PLL 1203 can once again lock. Power control 14 may be configured to provide gain control for Class E Driver 1202, and thus for mesh 1201. Note that a breath-actuated mode of operation as described herein may be used for different types of respiratory medicament delivery devices.

Figure 14:
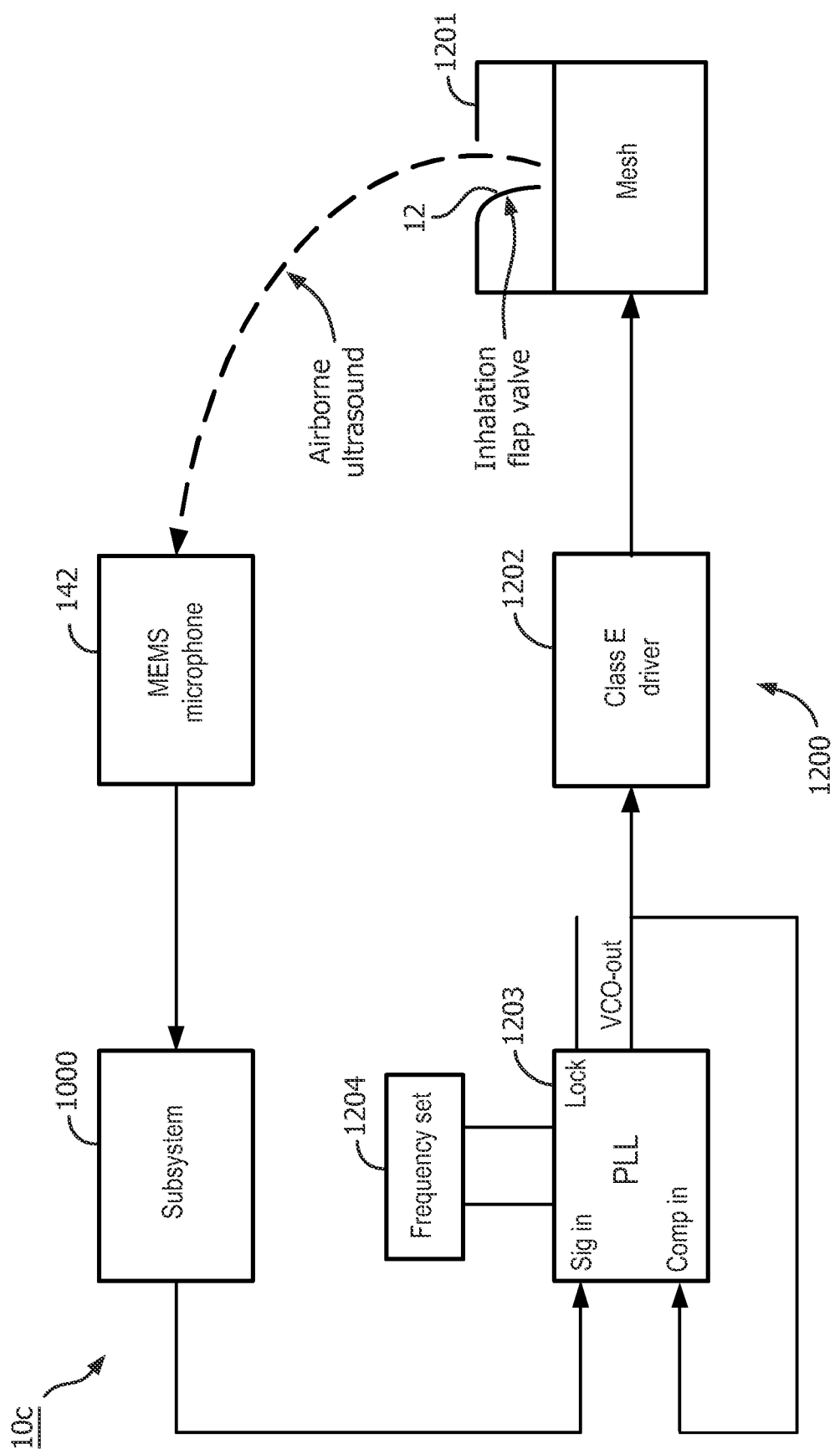

In some implementations, a system similar to system 10*b* in FIG. 13 may not need a power control such as power control 14. By way of illustration, FIG. 14 schematically illustrates a system 10*c*, similar to system 10*b* in FIG. 13, that includes an inhalation flap valve 12. When PLL 1203 is locked, it outputs the resonant frequency for mesh 1201. When PLL 1203 is not locked, it outputs a different frequency (e.g. an off-resonance frequency and/or one or more sub-harmonic frequencies of the resonance frequency) such that less or no aerosol is produced. A breath-actuated mode of operation may be applied for different types of respiratory medicament delivery devices.

Information derived from a graph such as graph 500 may be used to determine device actuation, respiratory rate, inhalation period, exhalation period, flow rate, strength of inhalation by a patient, amount of drug delivered, number of drug delivery sessions in a day or week, etc. Based on a comparison of such measured information and the recommended treatment for a subject, a level of patient adherence may be determined. Combination of different types of derived information is contemplated within the scope of this disclosure. For example, device actuation information may be combined with patient-specific respiratory information to determine patient adherence. Device actuation and/or detection of device actuation may characterize operating of respiratory medicament delivery device 11 and/or any component thereof.

Referring to FIG. 1, in some implementations, respiratory medicament delivery device 11 may include a metered-dose inhaler and/or components/features thereof. The emitted ultrasonic energy for meter-dose inhalers may be a (brief) wide-band signal. Such a signal may be measured using a subsystem such as subsystem 1000*a* in FIG. 11, but with jumper 1021 removed (and resistor R9 changed from 10 kOhm to 2 kOhm), and thereby not using product detector 1007 (FIG. 10) or local oscillator 1020 (FIG. 11). In this mode of operation, the subsystem may be suitable for wide-band signals between about 15 kHz and about 65 kHz. By way of illustration, FIG. 8 illustrates a graph 800 for energy emitted during the operation of a metered-dose inhaler. Graph 800 includes a waterfall display in the top half, and a magnitude (of energy amplitude) in the bottom half. The waterfall display shows time on the vertical axis and measured frequency (in kHz) in the horizontal axis. As depicted in FIG. 8, graph 800 includes a brief wide band signal 801 between about 15 kHz and about 25 kHz. Information derived from graphs such as graph 800 may be used to control operation of a respiratory medicament delivery device and/or monitor respiratory parameters (e.g. as indicative of patient adherence).

Returning to FIG. 1, electronic storage 130 of system 10 comprises electronic storage media that electronically stores information. The electronic storage media of electronic storage 130 may include one or both of system storage that is provided integrally (i.e., substantially non-removable) with system 10 and/or removable storage that is removably connectable to system 10 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 10 to function properly. For example, electronic storage 130 may record or store vectors of parameters based on the generated output signals, and/or other parameters (as discussed elsewhere herein), and/or other information. Electronic storage 130 may be a separate component within system 10, or electronic storage 130 may be provided integrally with one or more other components of system 10 (e.g., processor 110).

User interface 120 of system 10 in FIG. 1 is configured to provide an interface between system 10 and a user (e.g., a user 108, subject 106, a caregiver, a therapy decision-maker, etc.) through which the user can provide information to and receive information from system 10. This enables data, results, and/or instructions and any other communicable items, collectively referred to as "information," to be communicated between the user and system 10. An example of information that may be conveyed by user 108 to system 10 is patient-specific adherence information. An example of information that may be conveyed to user 108 is a report detailing adherence information for subject 106. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 10 from removable storage (e.g., a smart card, a flash drive, a removable disk, etc.) that enables the user(s) to customize system 10. Other exemplary input devices and techniques adapted for use with system 10 as user interface 120 include, but are not limited to, an RS-232 port, RF link, an IR link, modem (telephone, cable, Ethernet, internet or other). In short, any technique for communicating information with system 10 is contemplated as user interface 120.

Processor 110 of system 10 in FIG. 1 is configured to provide information processing capabilities in system 10. As such, processor 110 includes one or more of a digital processor, an analog processor, a digital circuit designed to process information, an analog circuit designed to process information, and/or other mechanisms for electronically processing information. Although processor 110 is shown in FIG. 1 as a single entity, this is for illustrative purposes only. In some embodiments, processor 110 includes a plurality of processing units.

As is shown in FIG. 1, processor 110 is configured to execute one or more computer program modules. The one or more computer program modules include one or more of parameter determination module 111, control module 112, and/or other modules. Processor 110 may be configured to execute modules 111-113 by software; hardware; firmware; some combination of software, hardware, and/or firmware; and/or other mechanisms for configuring processing capabilities on processor 110.

It should be appreciated that although modules 111-113 are illustrated in FIG. 1 as being co-located within a single processing unit, in embodiments in which processor 110 includes multiple processing units, one or more of modules 111-113 may be located remotely from the other modules. The description of the functionality provided by the different modules 111-113 described herein is for illustrative purposes, and is not intended to be limiting, as any of modules 111-113 may provide more or less functionality than is described. For example, one or more of modules 111-113 may be eliminated, and some or all of its functionality may be incorporated, shared, integrated into, and/or otherwise provided by other ones of modules 111-113. Note that processor 110 may be configured to execute one or more additional modules that may perform some or all of the functionality attributed below to one of modules 111-113.

Parameter determination module 111 of system 10 in FIG. 1 is configured to determine one or more parameters from output signals generated by sensor(s) 142. The one or more parameters may include a first spectral parameter, and/or other parameters. The first spectral parameter may indicate (magnitude of) energy amplitude in a first frequency band. For example, the first spectral parameter may indicate the amplitude of the ultrasonic energy received by microphone 142 as described elsewhere herein. The first spectral parameter may characterize operation of respiratory medicament delivery device 11. In some embodiments, parameter determination module 111 is configured to determine additional spectral parameters in a manner similar to the first spectral parameter, though, e.g., corresponding to other frequency bands.

Operation of parameter determination module 111 may be performed in an ongoing manner, for example at a particular sampling rate. The one or more parameters may be determined at different locations and/or positions within system 10 or near subject 106. In some embodiments, parameter determination module 111 may derive vectors of parameters in an ongoing manner during a period of monitoring subject 106. The vectors of the parameters may be based on vectors of generated output signals and/or other (vectors of) determined parameters.

Control module 112 is configured to control respiratory medicament delivery device 11 during operation. Operation of control module 112 may be based on one or more parameters determined by parameter determination module 111. Control by control module 112 may include adjustments, e.g. of the operating frequency, drive power, and/or any other adjustable operating conditions as described herein. Adjustments may be based on determined (spectral) parameters and/or generated output signals. Adjustments may be made such that a particular determined parameter, e.g. the first spectral parameter, is maintained at or above at or above a predetermined threshold level. In some implementations, such a threshold is predetermined at a percentage of the known maximum for the particular determined parameter. The predetermined percentage may be about 80%, about 90%, about 95%, about 97%, about 98%, about 99%, and/or another percentage. Adjustments may be made in an ongoing manner, for example at a particular sampling rate. Adjustments may be made in real-time or near-real-time. The rate of adjustment may be milliseconds, 0.5 second, 1 second, 2 seconds, 5 seconds, 10 seconds, 20 seconds, and/or another appropriate rate.

Adherence module 113 is configured to determine an adherence metric and/or an adherence parameter for subject 106. The adherence metric and/or adherence parameter may be based on one or more parameters determined by parameter determination module 111. For example, a particular adherence metric may be based on a combination of device actuation information and respiratory information/timing. An adherence metric and/or adherence parameter may for example be expressed as a percentage of perfect compliance with the recommended treatment. For example, if a particular patient scored a 90% adherence, such a score that may be considered by a care giver in determining a course of action. Alternatively, if a particular patient scored a low percentage of adherence, such a score may be considered relevant before the particular drug is deemed ineffective for that particular patient. Low scores may prompt a change in the chosen type of drug delivery device.

Figure 2:
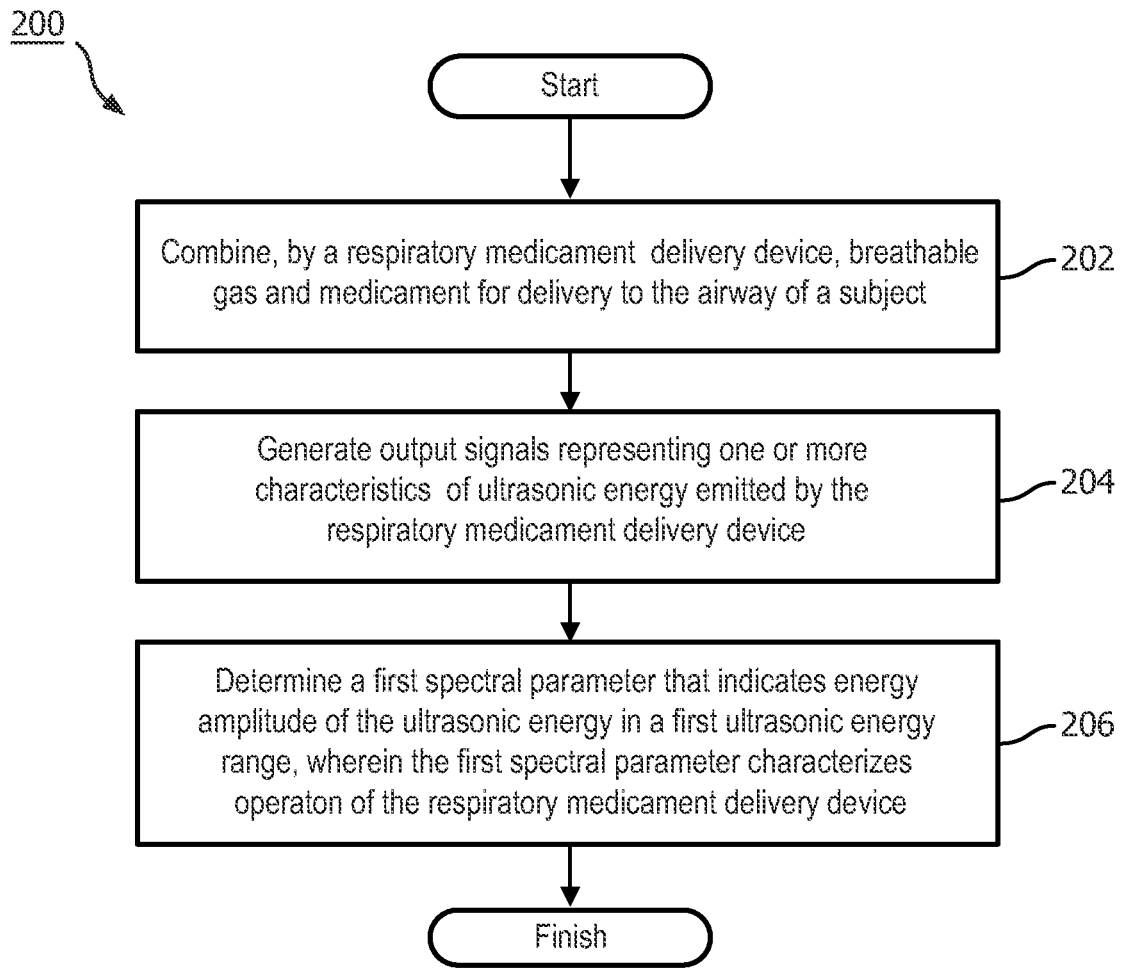
FIG. 2 illustrates a method of delivering medicament to a subject.

FIG. 2 illustrates a method 200 to deliver medicament to a subject. The operations of method 200 presented below are intended to be illustrative. In certain embodiments, method 200 may be accomplished with one or more additional operations not described, and/or without one or more of the operations discussed. Additionally, the order in which the operations of method 200 are illustrated in FIG. 2 and described below is not intended to be limiting.

In certain embodiments, method 200 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

At an operation 202, breathable gas and medicament are combined, by a respiratory medicament delivery device that emits ultrasonic energy during operation, for delivery to an airway of a subject. In some embodiments, operation 202 is performed by a respiratory medicament delivery device the same as or similar to respiratory medicament delivery device 11 (shown in FIG. 1 and described herein).

At an operation 204, output signals are generated that represent one or more characteristics of the ultrasonic energy emitted by the respiratory medicament delivery device. In some embodiments, operation 204 is performed by a sensor the same as or similar to sensor 142 (shown in FIG. 1 and described herein, also referred to as microphone 142).

At an operation 206, a first spectral parameter is determined that indicates energy amplitude of the ultrasonic energy emitted by the respiratory medicament delivery device during operation. The ultrasonic energy is emitted in a first ultrasonic frequency range. The first spectral parameter characterizes operation of the respiratory medicament delivery device. In some embodiments, operation 206 is performed by a parameter determination module the same as or similar to parameter determination module 111 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although this description includes details for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that, to the extent possible, one or more features of any embodiment are contemplated to be combined with one or more features of any other embodiment.

The invention claimed is:

1. A system configured to deliver medicament to a subject, the system comprising:
   a respiratory medicament delivery device configured to combine breathable gas and the medicament for delivery to an airway of a subject, wherein the respiratory medicament delivery device comprises a piezoelectric element having an operating frequency, and the respiratory medicament delivery device is configured to emit ultrasonic energy during operation;
   a sensor configured to generate output signals representing one or more characteristics of the ultrasonic energy emitted by the respiratory medicament delivery device during the operation; and
   one or more processors configured to execute computer program modules, the computer program modules comprising:
      a parameter determination module configured to determine, based on the generated output signals, a first spectral parameter that indicates an energy amplitude of the ultrasonic energy emitted by the piezoelectric element of the respiratory medicament delivery device during the operation in a first ultrasonic frequency range that includes the operating frequency of the piezoelectric element, such that the first spectral parameter characterizes the operation of the respiratory medicament delivery device.

2. The system of claim 1, further comprising:
   an inhalation flap valve configured to reduce ultrasonic energy received by the sensor during exhalation by the subject, wherein the parameter determination module is further configured to determine respiratory timing of the subject based on variations of the first spectral parameter, and wherein the control module is further configured to control the delivery of the medicament by the respiratory medicament delivery device based on the determined timing.

3. A system configured to deliver medicament to a subject, the system comprising:
   a respiratory medicament delivery device configured to combine breathable gas and the medicament for delivery to an airway of a subject and emit ultrasonic energy during operation, wherein the respiratory medicament delivery device further comprises a piezoelectric element having an operating frequency;
   a sensor configured to generate output signals representing one or more characteristics of the ultrasonic energy emitted by the respiratory medicament delivery device during the operation; and
   one or more processors configured to execute computer program modules, the computer program modules comprising:
      a parameter determination module configured to determine, based on the generated output signals, a first spectral parameter that indicates an energy amplitude of the ultrasonic energy emitted by the piezoelectric element of the respiratory medicament delivery device during the operation in a first ultrasonic frequency range that includes the operating frequency of the piezoelectric element, such that the first spectral parameter characterizes the operation of the respiratory medicament delivery device,
   wherein the respiratory medicament delivery device is one or both of a dry-powder inhaler and/or a metered-dose inhaler, the first spectral parameter characterizes the operation by indicating detection of actuation of the respiratory medicament delivery device, and the system further comprises:
      an adherence module that is configured to determine an adherence metric based on the first spectral parameter.

4. The system of claim 3, wherein the adherence module is further configured to determine the adherence metric as a percentage of perfect compliance with a recommended treatment based on the first spectral parameter.

5. A method of controlling delivery medicament to a subject, the method comprising;
   combining, by a respiratory medicament delivery device that emits ultrasonic energy during operation, breathable gas and medicament for delivery to an airway of a subject;
   generating, by a sensor, output signals representing one or more characteristics of the ultrasonic energy emitted by the respiratory medicament delivery device;
   determining a first spectral parameter that indicates energy amplitude of ultrasonic energy emitted by a piezoelectric element of the respiratory medicament delivery device during operation, wherein the ultrasonic energy is emitted in a first ultrasonic frequency range that includes an operating frequency of the piezoelectric element such that the first spectral parameter characterizes operation of the respiratory medicament delivery device.

6. The method of claim 5, further comprising:
   reducing, by an inhalation flap valve, ultrasonic energy received by the sensor during exhalation by the subject; and
   determining respiratory timing of the subject based on variations of the first spectral parameter, wherein controlling the respiratory medicament delivery device during operation is further based on the determined respiratory timing.

7. The method of claim 5, wherein the first spectral parameter characterizes operation by indicating detection of actuation of the respiratory medicament delivery device, the method further comprising determining an adherence metric based on the first spectral parameter.

8. A system configured to deliver medicament to a subject, the system comprising:
   means for combining breathable gas and medicament for delivery to an airway of a subject, wherein the means for combining emits ultrasonic energy during operation;

means for generating output signals representing one or more characteristics of the ultrasonic energy emitted by the means for combining;

means for determining a first spectral parameter that indicates energy amplitude of ultrasonic energy emitted by a piezoelectric element of the means for combining during operation, wherein the ultrasonic energy is emitted in a first ultrasonic frequency range that includes an operating frequency of the piezoelectric element such that the first spectral parameter characterizes operation of the means for combining.

9. The system of claim 8, further comprising:

means for reducing ultrasonic energy received by the sensor during exhalation by the subject; and means for determining respiratory timing of the subject based on variations of the first spectral parameter, wherein operation of the means for controlling is further based on the determined respiratory timing.

10. The system of claim 8, wherein the first spectral parameter characterizes operation by indicating detection of actuation of the respiratory medicament delivery device, the system further comprising for determining an adherence metric based on the first spectral parameter.

* * * * *